United States Patent [19]

Pietsch et al.

[11] 4,052,453
[45] Oct. 4, 1977

[54] PROCESS FOR PREPARING ACETOACETAMIDE-N-SULFOFLUORIDE

[75] Inventors: Hartmut Pietsch, Hofheim, Taunus; Karl Clauss, Rossert; Harald Jensen, Frankfurt am Main; Erwin Schmidt, Kelkheim, Taunus, all of Germany

[73] Assignee: Hoechst Aktiengesellschaft, Frankfurt am Main, Germany

[21] Appl. No.: 618,405

[22] Filed: Oct. 1, 1975

[30] Foreign Application Priority Data

Oct. 3, 1974 Germany .............................. 2447201

[51] Int. Cl.² ................. C07C 143/70; C07C 143/72
[52] U.S. Cl. ............................ 260/543 F; 260/556 R; 260/561 K
[58] Field of Search ........ 260/556 R, 556 AC, 561 K, 260/543 F

[56] References Cited

U.S. PATENT DOCUMENTS

| 2,174,239 | 9/1939 | Gleason ...................... 260/561 K X |
| 3,072,724 | 1/1963 | Elam et al. ................... 260/561 K |
| 3,526,663 | 9/1970 | Habib et al. .................. 260/561 K |
| 3,778,474 | 12/1973 | Stocker .......................... 260/561 K |

OTHER PUBLICATIONS

Petersen, Ber. 83, 551–559 (1950).
Diez et al., J. Heterocycl. Chem. 1973, 10(4), pp. 469–472.
Kato et al., CA 78:84162a (1973).
Erastor et al., CA 80:26674z (1974).
Lonza, Ltd., CA 59:7377d (1963).

Primary Examiner—Daniel E. Wyman
Assistant Examiner—Thomas A. Waltz
Attorney, Agent, or Firm—Curtis, Morris & Safford

[57] ABSTRACT

Process for preparing acetoacetamide-N-sulfofluoride by reacting amidosulfofluoride at a temperature of from 50° to 100° C with diketene, optionally in the presence of inert solvents or diluents.

7 Claims, No Drawings

PROCESS FOR PREPARING ACETOACETAMIDE-N-SULFOFLUORIDE

The present invention relates to a process for preparing acetoacetamide-N-sulfofluoride(I) by acetoacetylation of amidosulfofluoride (ASF) with diketene.

It is known to acetoacetylate weakly basic acid amides with diketene already in the presence of traces of tertiary amines or in glacial acetic acid (Houben-Weyl 7/4, 239; J. pharm. Soc. Japan 89, 1715 (1969)).

It is moreover known that the acetoacetylation of primary sulfonic acid amides in the form of their alkali salts may be carried out in aqueous solution with diketene. In the case of sulfoamidic acid and sulfamide the desired acetoacetylation products, however, could not be isolated hitherto. They could only be obtained in the form of their coupling products with 4-nitrophenyl-diazonium chloride. (Ber. 83, 551 (1959)).

These known methods cannot be transferred to the acetoacetylation of amidosulfofluoride (ASF) with diketene for the following reasons:

a. The desired reaction does not take place or only partially takes place under the indicated reaction conditions when using small quantities of tertiary amines or when operating in glacial acetic acid.
b. Instead of the attended reaction an immediate solvolysis of ASF in aqueous alkaline solutions can be observed.

The acetoacetylation product of ASF, namely acetoacetamide-N-sulfo-fluoride(I) could only be obtained hitherto from acetone, acetylacetone or acetoacetic acid tertiary butyl ester by reacting one of said substances with the toxic fluorosulfonylisocyanate (FSI), which can only be obtained with great difficulties (Angew. Chem. 85, 965 (1973)).

Methods enabling preparing (I) by acetoacetylation of ASF obtainable by a series of methods known in the literature have not become known hitherto.

The present invention consequently provides a process for preparing acetoacetamide-N-sulfofluoride of the formula(I)

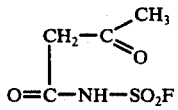

which comprises reacting amidosulfofluoride (ASF), preferably in the presence of an inert solvent or diluent, at temperatures of from 50° to 100° C, preferably of from 60° to 80° C, with diketene.

The reaction generally is carried out in the following manner: The starting components ASF and diketene are used in about stoichiometric quantitites, i.e. in a molar ratio of about 1:1, a small excess of up to 10% of one of both components being, however, possible. A higher excess of one of the components is likewise possible, certainly, but is of no especial advantage.

Owing to the fact that the reaction product acetoacetamide-N-sulfofluoride(I) has a melting point of from 86° to 88° C, one suitably operates in the presence of an inert solvent or diluent, especially with regard to the method of carrying out the reaction and the working up of the reaction mixture. The quantity of said solvent is not critical, but generally ranges from about 0.4 to 10 parts by weight, calculated on ASF used, preferably from 0.8 to 5 parts by weight.

The temperature range selected for the reaction of ASF with diketene is of decisive importance for the course of the reaction and the yield of the desired product (I). At temperatures below 50° C, approximately, the reaction, for example, is characterized by a too low reaction speed. The reaction speed considerably accelerates at temperatures in the range of from about 50° to 60° C and the reaction takes an exothermal course. The considerable heat developed is advantageously dissipated thereby by cooling, among others, for example, suitably by refluxing while using simultaneously inert solvents or diluents having a boiling temperature under the reaction conditions in the range of the reaction temperature. It is true that the reaction speed increases with an increasing reaction temperature, but an upper limit of the latter is given by the fact that aceto-acetamide-N-sulfofluoride (I) is thermally unstable and already begins to decompose at temperatures slightly above its melting point.

It is not recommended therefore to choose a reaction temperature higher than about 100° C, which would cause losses in yield of the product of the invention (I). The product (I) is obtained in a yield of about 50% of the theory according to the process of the invention.

Suitable solvents or diluents, for example, are: aliphatic and aromatic hydrocarbons such as pentane, hexane, cyclohexane, gasoline, petroleum ethers, benzene, toluene, xylene, ethers, for example, dimethyl ether, diethyl ether, diisopropyl ether, dimethoxyethane, tetrahydrofurane, dioxane, nitriles, for example, acetonitrile, halogenohydrocarbons, for example, methyl chloride, methylene chloride, chloroform, carbon tetrachloride or mixtures of such solvents. Solvents having a boiling point in the desired temperature range are preferably used. ASF and/or the reaction product possibly may precipitate as a second phase in the solvent used owing to their low solubility, but the reaction course is not influenced thereby, when mixing sufficiently enough. The reaction may also be carried out in the absence of solvents.

The reaction course can be observed by the infra-red spectrum, the characteristic bands of diketene disappearing at 5.2 to 5.3 μ.

The reaction according to the invention may be represented by the following scheme:

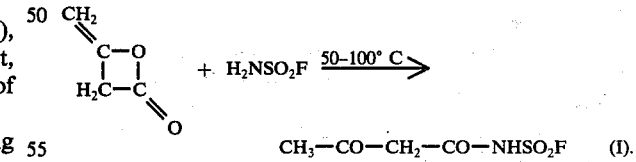

It is generally carried out in the following manner: The corresponding quantity of diketene is added to ASF firstly introduced, preferably in an inert solvent at the reaction temperature (the reflux temperature of the inert solvent optionally used simultaneously advantageously also corresponding thereto), advantageously while continuously mixing, for example, by stirring and/or refluxing of inert solvents or by flowing in a flow tube. The time of addition is not critical.

It essentially depends on the dissipation of the reaction heat and may be in the range of from 30 to 180 minutes, for example. When terminating the addition of diketene stirring of the reaction mixture is continued while maintaining the reaction temperature, until the characteristic bands of diketene at 5.2 to 5.3 μ disappear. The reaction mixture then is cooled and the reaction product (I) obtained in a crystalline form is filtered off with suction or the inert solvent optionally simultaneously used is evaporated previously in vacuo.

The crude product thus obtained may be directly converted into the sweetener 6-methyl-3,4-dihydro-1,2,3-oxathiazine-4-one-2,2-dioxide or its potassium salt, for example, with alkali according to the process of German Offenlegungsschrift No. 2,001,017 or preferably according to another process by reacting it with 2 moles of methanolic KOH. The latter process is used in the examples for determinating the yield.

The process of the invention may be carried out discontinuously or in simple manner continuously, for example, in a cascade apparatus or in a reaction tube. The reaction pressure is not critical, but the reaction is preferably carried out at atmospheric pressure. It may also be operated at reduced pressure or at elevated pressure, which may be advantageous in cases where the boiling temperature of inert solvents thus may reach the range of the reaction temperature in order to enable dissipating of the reaction heat by refluxing.

The following examples illustrate the invention.

EXAMPLE 1

84 g (1 mole) of diketene was added dropwise to a mixture of 99 g (1 mole) of amidosulfofluoride (ASF) and 100 ml of benzene boiling while refluxing within 30 minutes. After boiling for another 30 minutes the reaction mixture was cooled and the crystalline acetoacetamide-N-sulfofluoride (I) was filtered off with suction.

Yield:

For measuring the yield the crude product (I) liberated from the solvent was introduced without further purification into 500 ml of 4,4 normal methanolic potassium hydroxide solution, whereby the potassium salt of 6-methyl-3,4-dihydro-1,2,3-oxathiazine-4-one-2,2-dioxide precipitated, which then was isolated.
Yield: 48% of the theory.

EXAMPLE 2

99 g (1 mole) of ASF were added dropwise to 100 ml of diethyl ether and the mixture was heated, whereby a reflux was produced at 82° C. 84 g (1 mole) of diketene then were added dropwise. The boiling temperature of the mixture tell to 67° C in the course of the reaction. The mixture was allowed to react for 2 hours at the reflux temperature and the solvent was evaporated in vacuo. When cooling, the product (I) crystallized.
Yield: 47% of the theory (measured according to Example 1).

EXAMPLE 3:

99 g (1 mole) of ASF were added dropwise to 150 ml of diethyl ether and the mixture was heated subsequently, whereby a reflux was produced at 69° C. 84 g of (1 mole) of diketene were then added and the mixture was stirred. During the reaction the boiling temperature of the mixture tell to 58° C within 3 hours. The ether was evaporated in vacuo. (I) crystallized while cooling.
Yield: 46% of the theory (measured according to Example 1).

EXAMPLE 4:

84 g (1 mole) of diketene were added dropwise to a solution of 99 g (1 mole) of ASF in 100 ml of acetonitrile boiling at 82° C. Diketene had completely reacted after 2 hours. Acetonitrile was evaporated in vacuo. (I) crystallized when cooling.
Yield: 37% of the theory (measured according to Example 1).

EXAMPLE 5:

42 g (0.5 mole) of diketene were added dropwise to a solution of 49.5 g (0.5 mole) of ASF in 100 ml of ethyl acetate boiling while refluxing and heated for one hour while refluxing until diketene had been consumed. (I) crystallized after ethyl acetate had been evaporated in vacuo.
Yield: 46% of the theory (measured according to Example 1).

EXAMPLE 6:

84 g (1 mole) of diketene were added dropwise to a mixture of 99 g (1 mole) of ASF and 100 ml of chloroform boiling while refluxing and heated for 3 hours while refluxing until diketene had been consumed. (I) crystallized after evaporation of the chloroform.
Yield: 50% of the theory (measured according to Example 1).

EXAMPLE 7:

168 g (2 moles) of diketene were added dropwise to 198 g (2 moles) of ASF at a temperature of from 85° to 90° C while cooling. Diketene was consumed after the mixture had been stirred for 30 minutes at this temperature. (I) crystallized when cooling.
Yield: 49% of the theory (measured according to Example 1).

What is claimed is:

1. A process for the preparation of acetoacetamide-N-sulfofluoride of the formula (I)

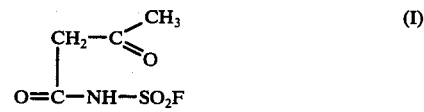

which comprises reacting amidosulfofluoride (ASF), in the liquid phase, at a temperature of from 50° to 100° C with diketene, in the presence of an inert diluent or solvent which is a member selected from the group consisting of aliphatic and aromatic hydrocarbons, ethers, nitriles and halogenohydrocarbons.

2. A process for the preparation of acetoacetamide-N-sulfofluoride of the formula (I)

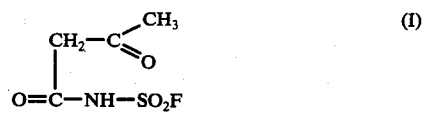

which comprises reacting amidosulfofluoride (ASF), in the liquid phase, at a temperature of from 50° to 100° C with diketene, in the presence of an inert diluent or solvent which is a member selected from the group consisting of pentane, hexane, cycylohexane, gasoline, petroleum ethers, benzene, toluene, xylene, dimethyl ether, diethyl ether, diisopropyl ether, dimethoxyethane, tetrahydrofurane, dioxane, acetonitrile, methyl chloride, methylene chloride, chloroform, carbon tetrachloride and mixtures thereof.

3. The process of claim 1, wherein the reaction temperature is in the range of from to 80°C.

4. The process of claim 1 which comprises carrying out the reaction in an inert diluent or solvent which is a member selected from the group consisting of benzene, diethyl ether, acetonitrile, ethyl acetate and chloroform.

5. The process of claim 1 wherein the inert diluent is used in an amount of from 0.4 to 10 parts by weight, based on the weight of amidosulfofluoride.

6. The process of claim 1 wherein the molar ratio of amidosulfofluoride to diketene is from 1:1.1 to 1.1:1.

7. A process for preparing acetoacetamide-N-sulfofluoride of the formula (I)

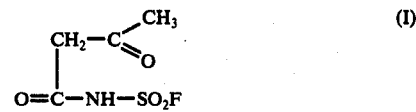

which comprises reacting amidosulfofluoride (ASF) at a temperature of from 50° to 100° C with diketene in the absence of a diluent or solvent.

* * * * *